United States Patent
Perrin

(10) Patent No.: US 10,449,038 B2
(45) Date of Patent: Oct. 22, 2019

(54) INTRA-LARYNGEAL PROSTHESIS COMPRISING A SEALING SKIRT

(71) Applicant: PROTIP MEDICAL, Strasbourg (FR)

(72) Inventor: Nicolas Perrin, Kolbsheim (FR)

(73) Assignee: PROTIP MEDICAL, Strasbourg (FR)

( * ) Notice: Subject to any disclaimer, the term of this patent is extended or adjusted under 35 U.S.C. 154(b) by 0 days.

(21) Appl. No.: 16/083,015

(22) PCT Filed: Mar. 8, 2017

(86) PCT No.: PCT/EP2017/055387
§ 371 (c)(1),
(2) Date: Sep. 7, 2018

(87) PCT Pub. No.: WO2017/153446
PCT Pub. Date: Sep. 14, 2017

(65) Prior Publication Data
US 2019/0110892 A1    Apr. 18, 2019

(30) Foreign Application Priority Data
Mar. 10, 2016   (FR) ..................................... 16 52035

(51) Int. Cl.
*A61F 2/20* (2006.01)
*A61B 17/24* (2006.01)

(52) U.S. Cl.
CPC .................................. *A61F 2/203* (2013.01)

(58) Field of Classification Search
CPC ............. A61F 2/203; A61F 2/20; A61B 17/24
USPC .......................................................... 623/9
See application file for complete search history.

(56) References Cited

U.S. PATENT DOCUMENTS

| 4,794,924 | A | 1/1989 | Eliachar |
| 8,551,168 | B2 | 10/2013 | Debry et al. |
| 9,913,713 | B2 * | 3/2018 | Perrin ........................ A61F 2/20 |
| 2004/0019387 | A1 | 1/2004 | Monnier et al. |
| 2005/0177233 | A1 | 8/2005 | Monnier et al. |
| 2009/0043386 | A1 * | 2/2009 | Persson ................... A61F 2/203 |
| | | | 623/9 |

(Continued)

FOREIGN PATENT DOCUMENTS

| EP | 0815807 A1 | 1/1998 |
| WO | 2009098408 A2 | 8/2009 |

(Continued)

OTHER PUBLICATIONS

International Search Report and Written Opinion dated May 17, 2017 for corresponding PCT Application No. PCT/EP2017/055387.

*Primary Examiner* — Suzette J Gherbi
(74) *Attorney, Agent, or Firm* — Polsinelli PC

(57) ABSTRACT

The invention relates to an intra-laryngeal prosthesis (PIL) for insertion into a larynx, said prosthesis PIL having an upper portion (PH) comprising: a tubular inner wall (1) with a first end, referred to as upper end (2), and a second end, referred to as lower end (3); a tubular outer wall (4) with a first end, referred to as upper end (2) and a second end, referred to as lower end (3), said outer wall (4) surrounding at least a portion of the inner wall (1); a plurality of ribs (5) extending in the direction of the main axis (X) of the prosthesis and connecting the inner wall (1) with the outer wall (4) such that a plurality of cells (6) are formed between the inner wall (1) and the outer wall (4).

18 Claims, 3 Drawing Sheets

(56) References Cited

U.S. PATENT DOCUMENTS

| | | | |
|---|---|---|---|
| 2009/0253099 A1* | 10/2009 | Debry | A61C 8/0012 |
| | | | 433/174 |
| 2010/0227294 A1* | 9/2010 | Takagi | A61C 8/005 |
| | | | 433/174 |
| 2011/0106251 A1 | 5/2011 | Debry et al. | |
| 2014/0288648 A1* | 9/2014 | Walder | A61F 2/203 |
| | | | 623/9 |
| 2015/0094809 A1* | 4/2015 | Perrin | A61F 2/203 |
| | | | 623/9 |
| 2016/0228239 A1* | 8/2016 | Perrin | A61F 2/20 |

FOREIGN PATENT DOCUMENTS

| | | |
|---|---|---|
| WO | 2013034858 A1 | 3/2013 |
| WO | 2015032886 A1 | 3/2015 |

* cited by examiner

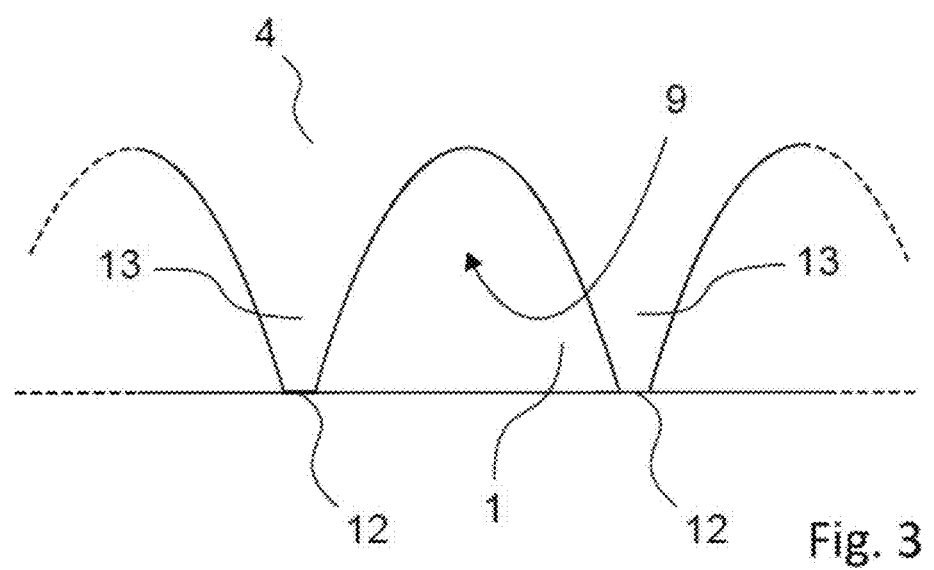

INTRA-LARYNGEAL PROSTHESIS COMPRISING A SEALING SKIRT

CROSS-REFERENCE TO RELATED APPLICATIONS

This application is a national stage application (under 35 U.S.C. § 371) of PCT/EP2017/055387, filed Mar. 8, 2017, which claims benefit of French Application No. 1652035, filed Mar. 10, 2016, which are incorporated herein by reference in their entireties.

TECHNICAL FIELD

The present invention concerns an intralaryngeal prosthesis. More particularly, the invention concerns an intralaryngeal prosthesis comprising a sealing skirt.

STATE OF THE PRIOR ART

One of the main functions of the larynx is to close off the lower airways (or respiratory tract) during swallowing to protect them and prevent the food bolus from entering, instead passing via the esophagus. This closing is done by a neuromuscular reflex mechanism of sequential closing of the larynx in four stages, going from bottom to top: vocal folds (glottis), ventricular bands, aryepiglottic folds and epiglottis. In the event of a malfunction in one of these stages, swallowing problems can result, because the larynx can no longer ensure correct protection of the lower airways, so that the food bolus could enter them (swallowing the wrong way) when it arrives at the crossroads of the respiratory and digestive tracts.

To remedy this problem, implanting an intralaryngeal prosthesis in the patient's larynx is known. Such a prosthesis is described, for example, in the document WO 2015/032886 that proposes an intralaryngeal prosthesis configured to be introduced into a larynx, the prosthesis having a tubular body having a proximal end surrounding a proximal opening and a distal end surrounding a distal opening, a valve having a proximal end and a distal end and a hinge connecting the proximal end of the valve to the proximal end of the tubular body so that the valve can be placed in a normal position in which it covers the proximal opening or in an open position in which it does not cover the proximal opening. In this device, the valve is arranged so that, in the normal position, the distal end of the valve forms a rim that covers a portion of the tubular body and that a space exists between the distal end of the valve and the tubular body so that air can enter the proximal opening of the tubular body by this space.

However, when a prosthesis according to the state of the art is introduced into a patient's larynx, sealing problems can occur between the prosthesis and the larynx. These problems are mainly due to a mismatch between the shape of the upper part of the prosthesis and the morphology of the patient's larynx, since this morphology can vary from one patient to another. These sealing problems lead to a penetration of the food bolus or saliva into the lower airways that can lead to discomfort or even infections of the lower airways (aspiration pneumonia).

There is therefore a need for an intralaryngeal prosthesis that ensures a good seal between the upper part of the prosthesis and the larynx.

DISCLOSURE OF THE INVENTION

The invention seeks to remedy this technical problem and, to do so, proposes an intralaryngeal prosthesis having an upper part comprising an inner wall and an outer wall connected by a plurality of ribs, this structure forming a sealing skirt to adapt the shape of the upper part of the prosthesis to the morphology of the larynx.

To do so, a first aspect of the invention concerns an intralaryngeal prosthesis intended to be introduced into a larynx; said prosthesis having a tubular lower part and an upper part, this upper part comprising:
- a tubular inner wall, comprising a first end, called upper end, and a second end, called lower end;
- a tubular outer wall comprising a first end, called upper end and a second end, called lower end; said outer wall surrounding the inner wall; the inner wall and outer wall connecting at both their first and second ends;
- a plurality of ribs extending along the direction of the main axis of the prosthesis and connecting the inner wall to the outer wall forming a plurality of cells between the inner wall and the outer wall;

the tubular lower part of the prosthesis being arranged in the extension of the tubular inner wall of the upper part of the prosthesis, thus forming a tubular conduit.

Thus, the prosthesis according to the invention ensures a better seal between the upper part of the prosthesis and the larynx. In fact, the outer wall adapts to the morphology of the larynx by deformation. Moreover, the presence of ribs and cells ensures good rigidity to the structure and allows local deformations not to affect the whole upper part of the prosthesis. The tubular conduit defines a distal opening in the lower part of the prosthesis and a proximal opening in the upper part of the prosthesis allowing the passage of air to the lower airways.

The intralaryngeal prosthesis described here can also have one or more of the characteristics below taken independently or according to all the technically-possible combinations.

Advantageously, each cell comprises an opening arranged at the lower end of the outer wall of the upper part of the prosthesis.

Thus, the risk of accumulating saliva or food bolus in the cells is eliminated. Moreover, this allows manufacturing the device by overmolding in a single step, since the orifices left by the mold used in this overmolding step, when positioned according to the invention, are not detrimental to the sealing of the prosthesis.

Advantageously, the junction between the outer wall and the inner wall at their lower ends, at the cell openings, is made by means of a plurality of anchoring strips, each terminating by an anchoring area and in that each opening is delimited by two anchoring strips, the width of the anchoring strips increasing further from the anchoring area. Preferably, each opening has the shape of an inverted U.

Thus, the risks of irritation or inflammation of tissues, especially of the vocal folds, are limited, since contact is made gradually by means of anchoring strips whose width increases further from the anchoring area.

Advantageously, the outer wall is essentially cylindrical and has a first protrusion, said protrusion extending over a part of the diameter and at least a part of the length of the outer wall.

Preferentially, the outer wall has a second protrusion diametrically opposed to the first protrusion, said second protrusion extending over a part of the diameter and at least a part of the length of the outer wall.

Diametrically opposed means that the projection in a plane perpendicular to the main axis of the prosthesis of the second protrusion is diametrically opposed (central symmetry with respect to the projection of the axis) to the projection of the first protrusion in this same plane. In other words, although diametrically opposed, the two protrusions can be located at a different height along the main axis of the prosthesis.

Thus, the shape of the prosthesis and, in particular, its upper part, follows the morphology of the larynx. The presence of these protrusions therefore allows reducing the discomfort felt by the patient while increasing the seal between the prosthesis and the larynx wall.

Advantageously, the thickness of the ribs and/or the thickness of the outer wall is comprised between 0.1 mm and 1 mm. Preferably, the rib thickness is essentially equal to 0.3 mm and the outer wall thickness is essentially equal to 0.4 mm. A good compromise is thus obtained between the necessary rigidity for good mechanical strength and the necessary flexibility for the outer wall and ribs to be able to adapt to the larynx morphology.

Advantageously, the proximal opening of the tubular conduit is sealed with a face seal, since lateral orifices can be positioned on the periphery of the upper part of the prosthesis around the face seal to ensure the passage of air such as the crenellated orifices described in EP 815 807.

In other embodiments, the proximal opening of the tubular conduit is sealed by valves, in particular the ones described in WO 2013/034858, WO 2009/098408 or WO 2015/032886.

Preferentially, the prosthesis according to the invention comprises a valve, the valve having:
a first part, called movable part, having a proximal end and a distal end;
a second part, called fixed part, having a proximal end, the fixed part being integral with the upper part of the prosthesis;
a hinge connecting the proximal end of the movable part to the proximal end of the fixed part so that the movable part of the valve can be placed in a normal position in which it covers the proximal opening of the tubular conduit or in an open position in which it does not cover the proximal opening of the tubular conduit.

Thus, the movable part, when it is in normal position, ensures the protective function of preventing the food bolus from entering into the larynx. Moreover, the surgeon can also open the valve to do a check of the airways, for example with an endoscope going into the prosthesis.

Advantageously, the movable part of the valve has a convex dome shape and the valve is arranged so that in the normal position the distal end of the movable part of the valve forms a rim with an area of the upper part of the prosthesis and that a space exists between the distal end of the movable part of the valve and the upper part of the prosthesis so that air can enter the proximal opening of the tubular conduit by this space.

Thus, the air circulates via the baffle-shaped space provided between the valve and the upper part of the prosthesis. Moreover, the fact that the movable part of the valve forms a rim with an area of the upper part of the prosthesis prevents saliva and the food bolus evacuated from the surface of the valve from being evacuated into the tubular conduit. However, to nevertheless allow air circulation, the movable part of the valve is configured so that a space exists between the movable part of the valve, and more precisely between its rim and the upper part of the prosthesis. Air can therefore enter into the tubular conduit by this space, without saliva or the food bolus entering into the tubular conduit because of the rim.

Advantageously, the movable part of the valve has a lower face, and the hinge is shaped (especially via a torsion spring exerting a return torque on the valve, or elastically) so that the valve is closed in the normal position when no force greater than a threshold force is exerted on the lower face of the valve, and that the movable part of the valve moves to the open position when a force greater than a threshold force is exerted on the lower face of the movable part of the valve.

Thus, in normal respiration, the valve remains in the normal position and therefore it covers the proximal opening of the tubular conduit so as to protect it. In the event of expectoration, the movable part of the valve opens to facilitate the patient's expiration. This is also the situation in case of coughing, sneezing or forced expiration.

A movable part of the valve can be made off-center relative to the upper part of the prosthesis so that:
the distal end of the movable part of the valve forms a rim that covers an area of the upper part of the prosthesis and that;
a space exists between the distal end of the movable part of the valve and the upper part of the prosthesis so that air can enter into the proximal opening of the tubular conduit by this space.

The movable part of the valve is preferably off-center in a direction opposite that of the hinge.

The movable part of the valve can also have transverse dimensions greater than those of the upper part of the prosthesis so that:
the distal end of the movable part of the valve forms a rim that covers an area of the upper part of the prosthesis and that;
a space exists between the distal end of the movable part of the valve and the upper part of the prosthesis so that air can enter into the proximal opening of the tubular conduit by this space.

Naturally, the two preceding embodiments can be performed separately or combined.

Advantageously, the valve is of titanium so as to prevent deformations of the fixed part of the valve when the hinge is deformed or of the movable part of the valve under the effect of the food bolus or saliva.

Advantageously, the movable part of the valve has centering means positioned on its lower face, the proximal end of the tubular conduit having complementary centering means, the centering means of the movable part of the valve being arranged to cooperate with the complementary means of the tubular conduit so as to ensure that the movable part of the valve returns to the desired position when it goes from the open position to the normal position. For this, the centering means can be formed by a truncated centering cone projecting from the lower face of the movable part of the valve. Complementary centering means can be formed in this case by a truncated conical orifice made in a transverse wall of the tubular conduit, the orifice being adapted to receive the centering cone. This technical solution ensures that the movable part of the valve returns to the normal position (closed), the covering between the valve and the titanium body being designed to prevent any body (bolus, saliva, etc.) from passing into the prosthesis by entering by the sides of the prosthesis, between the valve and the upper part of the prosthesis.

Advantageously, the movable part of the valve is elliptical so as to better adapt to the patient's anatomy and reduce the footprint as much as possible relative to surrounding anatomical structures.

Advantageously, the lower part of the prosthesis comprises protruding external projections, for fixing said prosthesis in position inside the larynx by supporting said projections against an inner wall of the larynx. Advantageously, the projections are chevron shaped. These projections allow the prosthesis to be properly held when it is in position in the larynx.

Advantageously, the upper part and lower part of the prosthesis are made of silicone and the fixed part of the valve is entirely embedded in the silicone making up the upper and lower part. The joining of the valve with the upper part is thus ensured.

Advantageously, the first protrusion is diametrically opposed to the valve hinge. This configuration ensures that the protrusion is located on the same side as the arytenoid cartilages. In this case, the extent of the first protrusion along the length of the outer wall, i.e., along the main axis of the prosthesis, is chosen so that, when the prosthesis is located in the larynx, the first protrusion is located opposite the arytenoid cartilages. Likewise, the extent of the second protrusion along the length of the outer wall, i.e., along the main axis of the prosthesis, is chosen so that, when the prosthesis is located in the larynx, the second protrusion is located in the space located just above the anterior commissure of the vocal folds.

Preferentially, all the materials used to create the intralaryngeal prosthesis are biocompatible.

BRIEF DESCRIPTION OF THE FIGURES

Other characteristics and advantages of the invention will result from reading the detailed description that follows, in reference to the attached figures, which illustrate:

FIG. 3, a detailed view of an opening of a cell according to the invention

For more clarity, identical or similar elements are called by identical reference signs in all the figures.

DETAILED DESCRIPTION OF AT LEAST ONE EMBODIMENT

Figure 1:
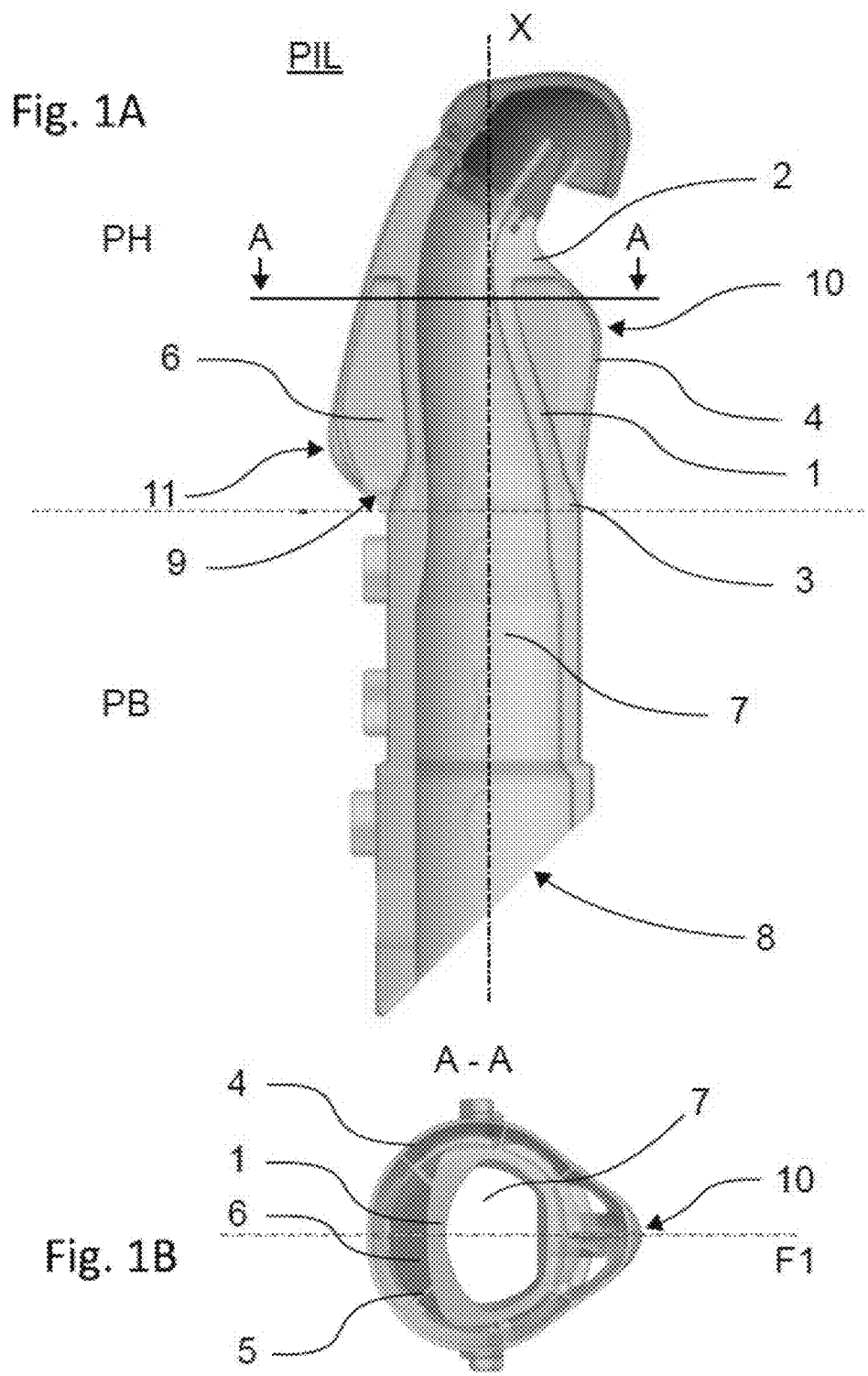
FIG. 1A, a side view in section of a prosthesis according to one embodiment of the invention.
FIG. 1B, a top view in section of a prosthesis according to one embodiment of the invention.
Figure 2:
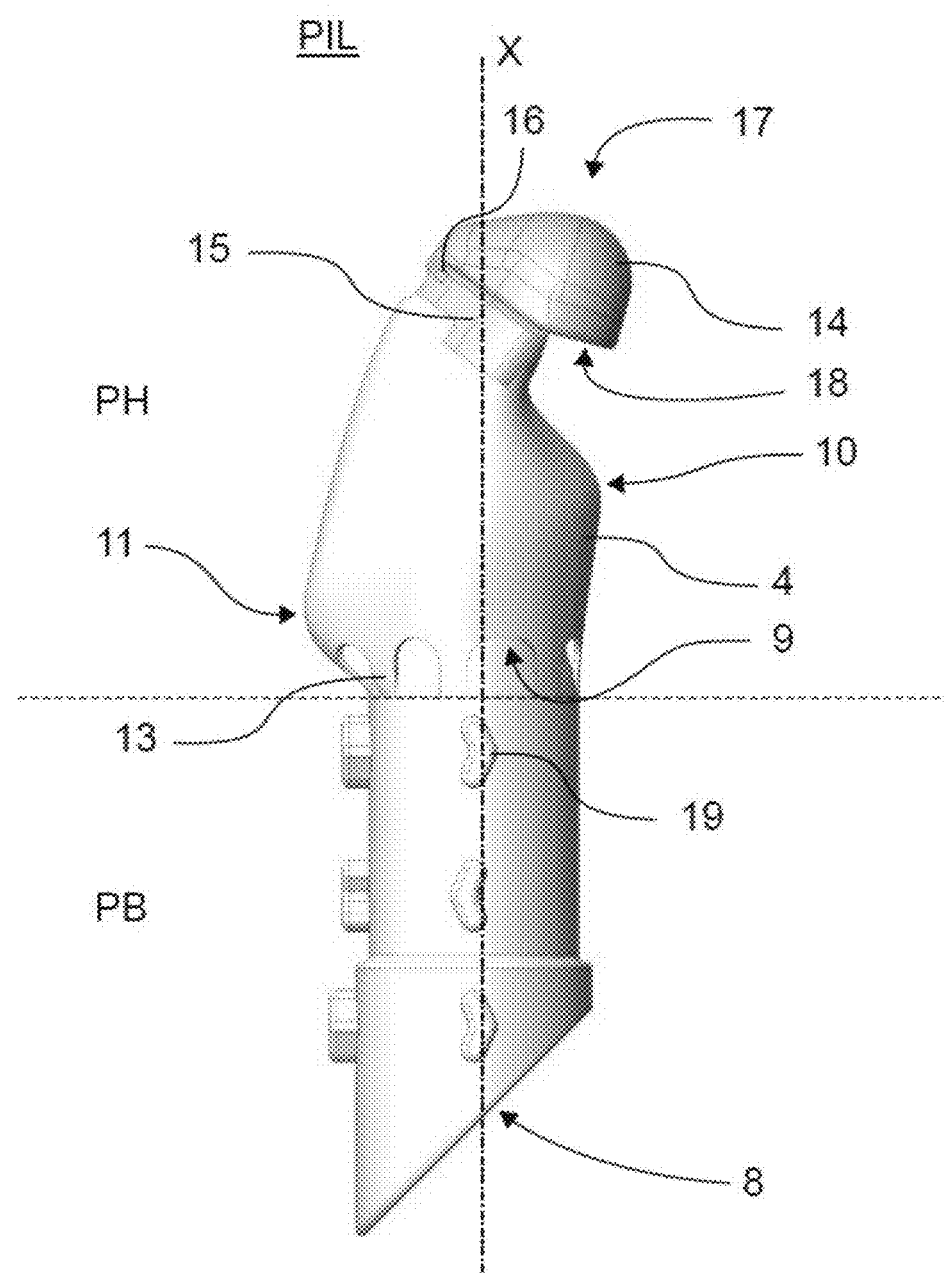
FIG. 2, a side view of a prosthesis according to one embodiment of the invention.

In a first embodiment illustrated in FIGS. 1A-B and 2, the intralaryngeal prosthesis ILP according to the invention has a tubular lower part LP and an upper part UP, the upper part UP comprising:
  a tubular inner wall 1 comprising a first end, called upper end 2, and a second end, called lower end 3;
  a tubular outer wall 4 comprising a first end, called upper end 2 and a second end, called lower end 3; said outer wall 4 surrounding the inner wall 1; the inner wall 1 and outer wall 4 connecting at both their first ends 1 and second ends 3;
  a plurality of ribs 5 extending along the direction of the main axis X of the prosthesis and connecting the inner wall 1 to the outer wall 4 forming a plurality of cells 6 between the inner wall 1 and the outer wall 4;
lower part LP of the prosthesis being positioned in the extension of the inner wall 1 of the upper part UP of the prosthesis, thus forming a tubular conduit 7.

Thus, the prosthesis ILP according to the invention ensures the seal between the upper part UP of the prosthesis ILP and the larynx, the outer wall 4 adapting by deformation to the morphology of the larynx. Moreover, the presence of ribs 5 and cells 6 ensures good rigidity to the outer wall and allows local deformations not to affect the whole upper part UP of the prosthesis ILP.

The tubular conduit 7 formed by the lower part LP of the prosthesis ILP and the inner wall 1 of the upper part UP of the prosthesis ILP defines a distal opening 8 in the lower part LP of the prosthesis and a proximal opening in the upper part of the prosthesis (not shown), opposite the distal opening 8, permitting air to circulate in the airways.

In the prosthesis according to the invention, it is also possible to modulate the mechanical strength of the outer wall 4 by changing the thickness of the ribs 5 and/or the thickness of the outer wall 4. In one embodiment, the thickness of the ribs 5 and/or the thickness of the outer wall 4 is comprised between 0.1 mm and 1 mm. Preferably, the rib 5 thickness is essentially equal to 0.3 mm and the outer wall 4 thickness is essentially equal to 0.4 mm. In one embodiment, the ribs 5 have a different thickness depending on their position.

In the embodiment illustrated in FIG. 1B, the ribs 5 are eight in number. However, a different number of ribs 5 can be envisaged. An embodiment in which the ribs 5 are three in number can particularly be envisaged. In one preferential embodiment, the ribs 5 are arranged symmetrically relative to a plane F1 going through the main axis X of the prosthesis ILP. When the prosthesis is positioned in the patient's larynx, plane F1 coincides with the sagittal plane.

In one embodiment, each cell 6 comprises an opening 9 arranged at the lower end 3 of the outer wall 4 of the upper part UP of the prosthesis ILP.

Indeed, in the case where the manufacturing technique for the prosthesis ILP according to the invention involves the use of a mold, this mold must be able to be extracted from the piece obtained. This extraction is generally done by openings, these openings resulting from the shape of the mold used. However, in the prosthesis ILP that is the subject of the invention, the arrangement of openings 9 is important, because an incorrect arrangement of these openings 9 can lead to an accumulation of saliva or the food bolus in the cells 6. By positioning the openings 9 at the lower end 3 of the inner wall 1 and outer wall 4, the risk of accumulation of saliva or the food bolus in the cells 6 is eliminated, since the elements likely to accumulate in the cells 6 are stopped by the outer wall 4 of the upper part UP of the prosthesis ILP.

However, the presence of these openings 9 can cause tissue irritation and, in particular, of the vocal folds which, when the prosthesis ILP is in place in the larynx, are found near the lower end 3 of the inner wall 1 and outer wall 4 of the upper part UP. This is especially the case if the openings 9 are present in the form of slots, the borders of the openings then being in the form of very marked edges.

In order to limit this irritation risk, in one embodiment illustrated in FIG. 3, the junction between the outer wall 4 and the inner wall 1 at their lower end 3 is made by means of a plurality of anchoring strips 13 each terminating by an anchoring area 12 and in that each opening 9 is delimited by two anchoring strips 13, the width of the anchoring strips 13 increasing further from the anchoring area 12.

This configuration limits tissue damage. Indeed, the flared shape of the anchoring strips 13 ensures gradual contact and limits tissue irritation at the lower end 3 of the outer wall 4 and inner wall 1 of the upper part UP. In one embodiment, each opening 9 has the shape of an inverted U.

The distance between the inner wall 1 and outer wall 4 can also vary. In one embodiment, the distance between the outer wall 4 and inner wall 1 is comprised between 0.5 mm and 10 mm. One can also choose to modulate the distance between the inner wall 1 and the outer wall 4 to form protrusions.

In one embodiment, the outer wall 4 is essentially cylindrical and has a first protrusion 10, said protrusion 10 extending over a part of the diameter and at least a part of the length of the outer wall 4 of the upper part of the prosthesis.

This protrusion 10 gives the prosthesis ILP a shape closer to the morphology of the larynx which permits reducing the discomfort caused by the prosthesis while increasing the seal between the larynx and the prosthesis ILP. In one embodiment, the shape and location of this first protrusion 10 are chosen so that, when the prosthesis ILP is in place in the larynx, the first protrusion 10 is located opposite the upper part of the arytenoid cartilages.

In one embodiment, a second protrusion 11 is provided diametrically opposed to the first protrusion 10, said second protrusion 11 extending over a part of the diameter and at least a part of the length of the outer wall 4 of the upper part of the prosthesis.

Diametrically opposed means that the projection in a plane perpendicular to the main axis X of the prosthesis ILP of the second protrusion 11 is diametrically opposed, relative to the diameter of the tubular conduit 7, to the projection of the first protrusion 10 in this same plane. In other words, although diametrically opposed, the two protrusions 10, 11 can be located at a different height along the main axis X of the prosthesis ILP.

Like the first protrusion 10, this second protrusion 11 gives the prosthesis ILP a shape closer to the morphology of the larynx which permits reducing the discomfort caused by the prosthesis ILP while increasing the seal between the larynx and the prosthesis ILP. In one embodiment, the shape and location of this second protrusion 11 are chosen so that, when the prosthesis ILP is in the larynx, the second protrusion 11 is located at the space located just above the anterior commissure of the vocal folds.

This adaptation of the protrusions to the morphology of the larynx is also improved by the presence of the ribs and cells 6 that allows the local deformation of these protrusions 10, 11 and helps to obtain a good adaptation of the prosthesis ILP while reducing the discomfort experienced by the patient.

In one preferential embodiment, the first protrusion 10 and second protrusion 11 are chosen so as to have the same plane of symmetry as the larynx when the prosthesis is in place in said larynx. In other words, once in the larynx, the sagittal plane is a plane of symmetry of the first protrusion 10 and second protrusion 11. In another embodiment, the ribs 5 are positioned symmetrically relative to the plane of symmetry of the first protrusion 10 and second protrusion 11.

In one embodiment, the lower part LP of the prosthesis ILP comprises protruding external projections 19, for fixing said prosthesis ILP in position inside the larynx by supporting said projections 19 against an inner wall of the larynx. Advantageously, the projections 19 are chevron shaped. These projections 19 allow the prosthesis ILP to be properly held when it is in position in the larynx.

In one embodiment, the prosthesis comprises a valve 17, the valve 17 having:
a first part, called movable part 14, having a proximal end and a distal end;
a second part, called fixed part 15, having a proximal end, the fixed part 15 being integral with the upper part UP;
a hinge 16 connecting the proximal end of the movable part 14 to the proximal end of the fixed part 15 so that the movable part 14 of the valve can be placed in a normal position in which it covers the proximal opening of the tubular conduit 7 or in an open position in which it does not cover the proximal opening of the tubular conduit 7.

In one embodiment, the movable part 14 of the valve 17 has a convex dome shape and the valve 17 is arranged so that in the normal position the distal end of the movable part 14 of the valve 17 forms a rim 18 with an area of the upper part UP of the prosthesis ILP and that a space exists between the distal end of the movable part 14 of the valve and the upper part UP of the prosthesis ILP so that air can enter the proximal opening of the tubular conduit 7 by this space.

Thus, the fact that the movable part of the valve 17 forms a rim that covers a part of the tubular conduit 7 prevents saliva and the food bolus evacuated from the surface of the movable part of the valve 17 from being evacuated into the tubular conduit 7 and therefore into the lower airways. However, to allow air circulation despite everything, the movable part of the valve 17 is configured so that a space exists between the movable part of the valve 17, and more precisely between its rim 18 and the upper part UP of the prosthesis ILP. Air can therefore enter into the tubular conduit 7 by this space, without saliva or the food bolus entering into the tubular conduit because of the rim 18.

The invention claimed is:

1. An intralaryngeal prosthesis (ILP) intended to be introduced into a larynx; said prosthesis having an upper part (UP) comprising:
a tubular inner wall (1) comprising a first end, called upper end (2), and a second end, called lower end (3);
a tubular outer wall (4) comprising a first end, called upper end (2) and a second end, called lower end (3), said outer wall (4) surrounding at least a portion of the inner wall (1);
a plurality of ribs (5) extending along the direction of the main axis (X) of the prosthesis and connecting the inner wall (1) to the outer wall (4) forming a plurality of cells (6) between the inner wall (1) and the outer wall (4).

2. The intralaryngeal prosthesis of claim 1, which also comprises a tubular lower part (LP), positioned in the extension of the inner wall (1) of the upper part (UP) of the prosthesis, thus forming a tubular conduit (7).

3. The intralaryngeal prosthesis of claim 1, wherein the upper end (2) is closed.

4. The intralaryngeal prosthesis of claim 1, wherein the upper end (2) is open.

5. The intralaryngeal prosthesis of claim 3, wherein the prosthesis has a tubular lower part, positioned in the extension of the inner wall (1) of the upper part (UP) of the prosthesis, and said tubular part has an opening located that it is aligned with the tracheotomy opening after implantation of the prosthesis in the larynx.

6. The intralaryngeal prosthesis of claim 1, wherein each cell (6) comprises an opening (9) arranged in the lower end (3) of the outer wall (4) of the upper part (UP) of the prosthesis.

7. The intralaryngeal prosthesis of claim 2, wherein the junction between the outer wall (4) and the inner wall (1) at their lower end (3) is made by means of a plurality of anchoring strips (13) each terminating by an anchoring area (12) and in that each opening (9) is delimited by two anchoring zones (13), the width of the anchoring strips (13) increasing further from the anchoring area (12).

8. The intralaryngeal prosthesis of claim 3, wherein each opening (9) has the shape of an inverted U.

9. The intralaryngeal prosthesis of claim 1, wherein the outer wall (4) is essentially cylindrical and has a first protrusion (10), said protrusion (10) extending over a part of the diameter and at least a part of the length of the outer wall (4).

10. The intralaryngeal prosthesis of claim 9, wherein the outer wall has a second protrusion (11) diametrically opposed to the first protrusion (10), said second protrusion (11) extending over a part of the diameter and at least a part of the length of the outer wall (4).

11. The intralaryngeal prosthesis of claim 1, wherein the thickness of the ribs (5) and/or the thickness of the outer wall (4) is comprised between 0.1 mm and 1 mm, preferably the rib thickness is essentially equal to 0.3 mm and the outer wall thickness is essentially equal to 0.4 mm.

12. The intralaryngeal prosthesis (ILP) of claim 2, wherein the tubular conduit (7) defines a proximal opening in the upper part (UP) of the prosthesis (ILP) and in that said prosthesis (ILP) comprises a valve (17), the valve (17) having:
   a first part, called movable part (14), having a proximal end and a distal end;
   a second part, called fixed part (15), having a proximal end, the fixed part (15) being integral with the upper part (UP);
   a hinge (16) connecting the proximal end of the movable part (14) to the proximal end of the fixed part (15) so that the movable part of the valve (14) can be placed in a normal position in which it covers the proximal opening of the tubular conduit (7) or in an open position in which it does not cover the proximal opening of the tubular conduit (7).

13. The intralaryngeal prosthesis of claim 12, wherein the movable part (14) of the valve has a convex dome shape and the valve is arranged so that, in the normal position, the distal end of the movable part (14) of the valve forms a rim (18) with an area of the upper part (UP) and that a space exists between the distal end of the movable part (14) of the valve and the upper part (UP) so that air can enter the proximal opening of the tubular conduit (7) by this space.

14. The intralaryngeal prosthesis of claim 12, wherein the outer wall (4) is essentially cylindrical and has a first protrusion (10), said protrusion (10) extending over a part of the diameter and at least a part of the length of the outer wall (4) and the first protrusion (10) is diametrically opposed to the hinge (16) of the valve.

15. The intralaryngeal prosthesis of claim 1, wherein the outer surface of the tubular outer wall (4) is smooth and/or covered with a surface coating preventing the adhesion of dust, mucus or moisture.

16. A method for treating a patient in need thereof, comprising the step of implanting the intralaryngeal prosthesis of claim 1 in the larynx of the patient.

17. A method for treating a patient in need thereof, comprising the step of implanting the intralaryngeal prosthesis of claim 2 in the larynx of the patient.

18. A method for treating a patient in need thereof, comprising the step of implanting the intralaryngeal prosthesis of claim 12 in the larynx of the patient.

* * * * *